United States Patent [19]
Alflen et al.

[11] Patent Number: 6,096,296
[45] Date of Patent: Aug. 1, 2000

[54] METHOD AND APPARATUS FOR A WIDE STICK CRYSTALLINE DEODORANT

[76] Inventors: Theodore Alflen, 960 NE. 27$^{th}$ Ave., Pompano Beach, Fla. 33062; William Miller, 1735 Camiento Ardiente, La Jolla, Calif. 92037

[21] Appl. No.: 08/957,644

[22] Filed: Oct. 24, 1997

Related U.S. Application Data

[60] Provisional application No. 60/029,782, Oct. 25, 1996.

[51] Int. Cl.$^7$ ........................................................ A61K 7/32
[52] U.S. Cl. ................................ 424/65; 424/68; 401/82; 401/84; 401/87; 401/88; 401/89; 401/95
[58] Field of Search .............................. 424/65, 68, 484; 401/82, 84, 87, 88, 89, 95

[56] References Cited

U.S. PATENT DOCUMENTS

| | | | |
|---|---|---|---|
| 3,789,857 | 2/1974 | Ikeda et al. | 132/88.7 |
| 4,595,124 | 6/1986 | Duval et al. | 222/39 |
| 4,879,116 | 11/1989 | Fox et al. | 424/682 |
| 5,076,720 | 12/1991 | Roger | 401/75 |
| 5,286,126 | 2/1994 | Harris et al. | 401/82 |
| 5,348,735 | 9/1994 | Harris et al. | 424/65 |
| 5,718,865 | 2/1998 | Askew | 264/331.11 |

OTHER PUBLICATIONS

Harry, The Principles and Practice of Modern Cosmetics, 1962, vol. 1, pp. 471–481.

H. Bennett, The Cosmetic Formulary, 1941, pp. 54 to 56 and 63.

Pharmaceutical Formulas, 1946, 10$^{th}$ edition, vo. II, pp. 109, 150–153, 304 and 305.

*Primary Examiner*—Jose' G. Dees
*Assistant Examiner*—Michael A. Williamson
*Attorney, Agent, or Firm*—Neil D. Greenstein; Techmark

[57] ABSTRACT

A shaped crystalline deodorant is made from mixture of a mineral salt and water which is heated above the melting point of the salt, placed in a mold having the desired shape, and crystalized after insertion of an internally threaded member into the mixture. The deodorant has an oval cross-sectional shape with the insert imbedded therewithin and is secured into a container. The container includes a threaded stem attached to the container for rotational movement which is translated to axial movement of the deodorant with respect to the container. The threaded stem cooperates with the internally threaded insert to allow the crystallized deodorant to be moved up or down within the container by rotating the threaded stem.

20 Claims, 3 Drawing Sheets

METHOD AND APPARATUS FOR A WIDE STICK CRYSTALLINE DEODORANT

CROSS REFERENCE TO RELATED APPLICATIONS

This application claims the benefits including priority rights of U.S. Provisional Application Ser. No. 60/029,782 filed Oct. 25 1996.

BACKGROUND OF THE INVENTION

1. Field of the Invention

This invention relates generally to crystalline deodorant systems and methods and more particularly to unitary shaped crystalline deodorants bars positionally secured in deodorant containing dispensers and methods for fabricating selected shaped and oval crystalline deodorant structures having tubular vertical inserts cooperably engagable with a rotable axial drive mechanism linked to a containing dispenser.

2. Description of the Prior Art

Crystalline or crystal deodorant systems have been fabricated for personal use to eliminate the odor of human perspiration for many years. Such deodorant systems contain deodorant bars which may include mineral salts such as potassium alum to eliminate or retard the formation of odor-causing bacteria. Such a deodorant eliminates or prevents the undesired human odor rather than merely masking it with a perfume or other desired substance. Crystalline deodorants differ from common antiperspirants which prevent the natural body function of perspiring. A crystalline deodorant is applied to a person's skin by rubbing it and leaving a thin film deposited at the situs of application. Before the crystalline deodorant works, however, it must be wetted with water to dissolve a small amount of the salt material contained in the deodorant. Crystalline deodorants are particularly effective and desirable because they are natural and devoid of undesirable additives. Accordingly, crystalline deodorants are effectively marketable to users who want a natural deodorant. Since crystalline deodorants have crystal structures, an initial commercial use of the deodorants was in the form of crystalline rock. Large crystals were accordingly formed during manufacturing and broken into smaller pieces having irregular shapes and sharp edges. The rough, sharp edges were removed, either manually or by tumbling action, for example, during manufacturing to create smooth bars acceptable to consumers. A smoothed crystalline deodorant rock or bar was thus marketed in a pouch, for example, or in a container or dish to hold the crystalline rock before and after use. Such deodorant products were intended for use on a counter in a bathroom, for example, for the convenience of the user.

SUMMARY OF THE INVENTION

According to one embodiment of the present invention, a crystalline deodorant is fabricated with an oval shape which is mounted in a twist-up container. According to another embodiment of the present invention, a crystalline deodorant is fabricated with a shape which is less or not subject to cracking when being made or used. According to a further embodiment of the present invention, an interface between the crystal deodorant and a twist-up mechanism secures the crystal to the twist-up mechanism so as to permit up and down movement of the crystal bar without cracking its unitary structure.

According to yet another embodiment of the present invention, potassium alum or another selected mineral salt is manufactured into a powder which is mixed with water or another solvent to create a slurry. The slurry is then heated to melt the mineral salt. The heated slurry is poured into a mold having a desired shape according to the present invention and having a cylindrical insert with internal threads or another externally engagable member inserted within the mold prior to pouring the slurry into the mold. The slurry is allowed to crystallize within the mold and secures itself around the insert. The insert is specifically adapted to be engagable with a complementary or threaded stem attached to a shaped container, which according to one embodiment is oval in cross-section. The threaded stem according to one embodiment of the present invention is rotatable by twisting a knob or similar extension element at the bottom of the container. When the crystal deodorant is placed to the container, a crystalline deodorant dispenser package according to the present invention is achieved.

BRIEF DESCRIPTION OF THE DRAWINGS

Various other objects, advantages and features of the present invention will become apparent to those skilled in the art from the following discussion taken in conjunction with the following drawings in which.

DETAILED DESCRIPTION OF THE PREFERRED EMBODIMENTS

As required by law, detailed embodiments of the present invention are disclosed herein. However, it is to be understood that the disclosed embodiments are merely exemplary of the invention which may be embodied in forms other than those specifically detailed herein. Therefore, the particular structural and functional details disclosed herein are not to be interpreted as exclusive or limiting, but merely as an exemplary basis for the claims below and as a representative basis for teaching one skilled in the art how to variously employ the present invention in particular implementations which are by no means exhaustive of the scope of the present invention.

Figure 1:
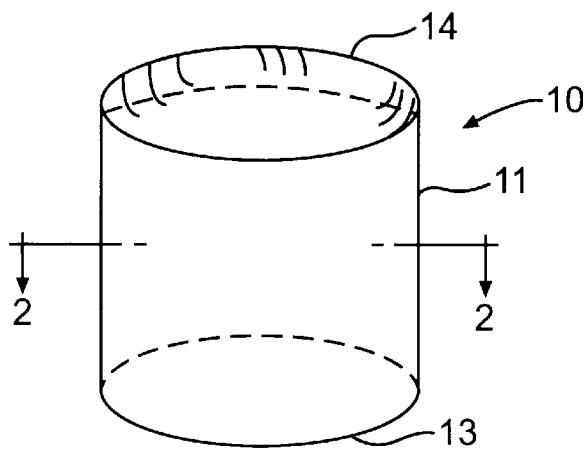
FIG. 1 is an isometric drawing of an oval crystalline deodorant in accordance with one embodiment of the present invention.

Referring now to FIG. 1, there is shown an isometric drawing of a unitary crystal or crystalline deodorant 10 in accordance with one embodiment of the present invention. The crystal deodorant 10, according to a first embodiment, is a unitary (i.e., one-piece) elongated member, stick, or bar structure 11 according to one embodiment of the present invention. According to this embodiment, the structure 11 has an oval, ellipsoidal, or rounded cross-sectional shape.

Figure 2:
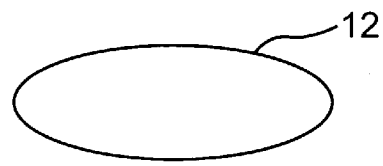
FIG. 2 is a horizontal cross sectional diagram of the structure of FIG. 1 taken along the line 2—2 of FIG. 1.

Referring now to FIG. 2, there is shown a horizontal cross sectional diagram of an oval cross-section embodiment of the structure 11 shown in FIG. 1. According to another embodiment of the present invention, the deodorant structure is substantially cylindrical. According to yet another embodiment of the present invention, the sides of the elongated structure 11 are flat. The bottom surface 13 of the elongated member, stick, or bar 11 is flat according to one embodiment, while the top surface 14 of the elongated member or bar 11 is rounded. The crystal deodorant 10 according to one embodiment of the present invention includes a crystalline structure made from a mixture of water and a powdered mineral salt such as potassium alum, for example, without limitation. to make the elongated member, stick, or bar 11. A predetermined amount of powdered potassium alum is mixed with water or another solvent at room temperature, for example, to make a predetermined amount of slurry material. The slurry material is then mixed and heated to a selected temperature above the melting point of the mineral salt, for example, thereby dissolving the salt in water.

Figure 3:
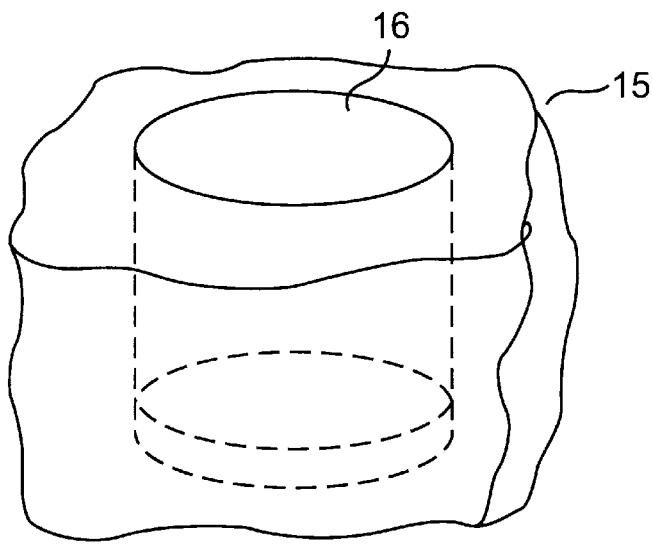
FIG. 3 is a schematic diagram of a single cavity mold of a type which may be used to cast an oval shaped deodorant structure according to the present invention.

FIG. 3 is a schematic diagram of a single cavity mold structure 15 of a type which is used to cast an oval or other rounded or flat shape deodorant bar or structure according to the present invention. The mixture of slurry material which has been prepared is poured, according to the present invention, while still hot, into a pre-configured mold structure 15 defining a predetermined interior surface 16 according to the desired finished shape of the crystal deodorant 10 which has been constructed according to the present invention.

Figure 4:
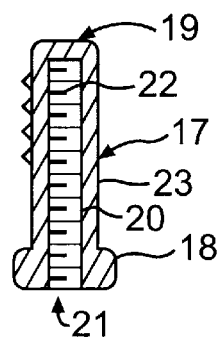
FIG. 4 is a cross-sectional diagram of a threaded insert which is fitable within an oval shaped deodorant structure according to the present invention.

FIG. 4 is a cross-sectional diagram of a tubular insert 17 into the molded bar structure which is hollow and internally continuously singly threaded and fitable within the shaped deodorant structure according to one embodiment of the present invention. In particular, tubular insert 17 includes a rounded or beveled closed end 19, cylindrical inner and outer walls respectively 20 and 23, and a lower flange 18 extending radially outward from the central axis of tubular insert 17. According to another embodiment of the present invention, tubular insert 17 is flangeless and has an open upper end 19 having a locking tab or flange to secure the insert within the molded bar structure. According to another embodiment of the present invention, the cylindrical inner wall 20 defines an inner surface which is multiply threaded with plural parallel threads running helically along the inner hollow surface of insert 17. According to even another embodiment of the present invention, only a selected portion of the hollow inner surface of insert 17 is threaded. The outer surface of insert 17 according to the present invention is irregular or ribbed or endowed with hills in one instance, permitting crystal molded around insert 17 to be held securely in place without lateral and axial movement upon completion of fabrication. According to another embodiment of the present invention, insert 17 is internally discontinually ribbed as opposed to being threaded with the ribs extending only partly around the inner diameter of insert 17. The insert 17 is introduced into the mold during construction at a selected location on the bottom surface 13 of the deodorant structure 10. Suitable means are utilized to suspend insert 17 within the mold during fabrication, and to center it within shape 12. A bottom flange 18 attached to insert 17 may be used to limit the insertion of insert 17 within the mixture within mold 15. The mixture is then allowed to cool, resulting in crystallization of the mineral salt. Such crystallization fixedly imbeds insert 17 within the oval shaped crystalline member 11. The resulting structure of the deodorant stick 11 according to the present invention is homogenous and resistant to cracking effects.

Tubular insert 17 comprises a plastic tube which is substantially cylindrical according to one embodiment of the present invention. The inserted end or top end 19 of tubular insert 17 is closed in order to prevent the mineral salt and water mixture from entering insert 17 during molding operation and fabrication of the crystal deodorant. Tubular insert 17 includes an axial channel 21 which is open at flange end 18 and closed at top end 19, according to one embodiment of the present invention. Axial channel 21 is internally threaded 22 according to one embodiment of the present invention. Flange member 18 is integrally constructed with insert 17 as a unitary member. Flange member 18 extends radially outward from the cylindrical surface of insert 17. The external surface 23 is patterned, irregular, or rough, according to the present invention, to ensure that insert 17 remains secured within the deodorant structure 11 during application by a user. Following crystallization and cool-down according to the present invention for a predetermined period of time, crystal deodorant 11 is removed from the mold 15 at the completion of a first phase of manufacture, and appears as schematically shown in FIG. 5 from a side cross-sectional view.

Figure 5:
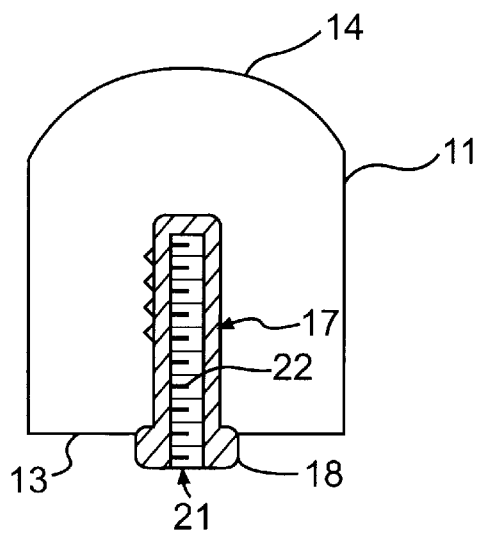
FIG. 5 is a cross-sectional diagram of the oval shaped deodorant structure fitted with an insert according to FIG. 4.

FIG. 5 is particularly a cross-sectional diagram of the crystal deodorant 11 fitted with a tubular insert 17 according to the present invention. To complete manufacture of the crystal deodorant 11, it is then fitted into a container 24 constructed according to the present invention. Container 24 for example comprises an oval shape in a transverse direction to a longitudinal axis as shown in FIG. 7.

Figure 6:
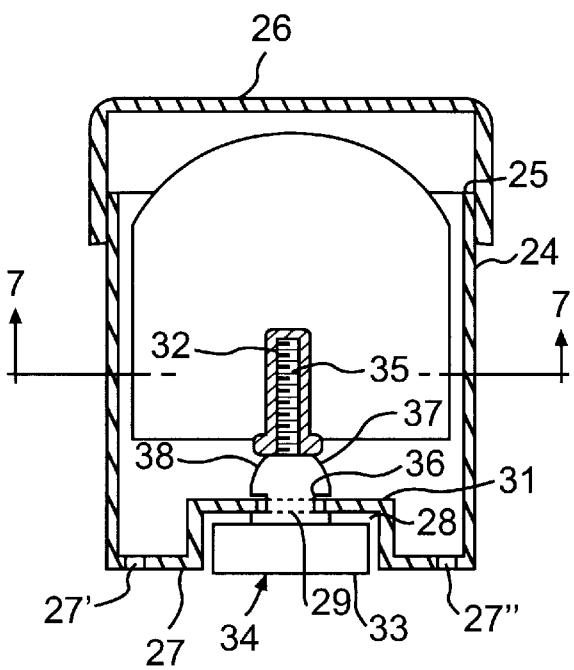
FIG. 6 is a vertical cross-sectional diagram of a twist-up container with a crystalline deodorant structure according to the present invention inserted therewithin.
Figure 7:
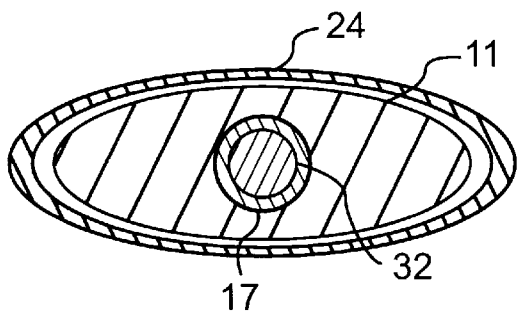
FIG. 7 is a horizontal cross-sectional diagram of the twist-up container and deodorant structure according to the present invention, taken along line 7—7 of FIG. 6.

FIG. 7 is a horizontal cross-sectional diagram of the twist-up container and deodorant structure according to the present invention, taken along line 7—7 of FIG. 6. The inner dimensions of deodorant container 24 are larger than the outer dimensions of crystal deodorant 11, enabling the crystal deodorant 11 to smoothly slide axially into and out of container 24 to a predetermined extent without getting stuck, permitting repeated user operation to make the deodorant ready for use and to withdraw the crystal deodorant 11 back into container 24 at the completion of use, to permit temporary storage of the container 24.

Container 24 includes an open upper end 25. A cap 26 is provided and proportioned to fit over the open upper end 25 of container 24. The bottom end 27 is flat but includes an indentation to form a crevice 28. A through hole 29 is provided through the thickness of the flat surface 31 of crevice 28. A rotatable member 34 is proportioned to be fitted within hole 29 and attached to the oval stick deodorant 11 so as to move the oval stick 11 up and down within container 24. Rotatable member 34 comprises a stem 32, a center portion 38 and a circular disk 33. Stem 32 has external threads 35 consistent with the threads 22 within insert 17. An annular cut-out or groove 36 is provided around center portion 38 and between disk member 33 and stem 32. A tapered lead-in configuration 37 is provided between groove 36 and stem 32. Upon insertion of stem 32 of rotatable member 34 into hole 29, the lead-in configuration 37 in conjunction with the elasticity of the material from which container 24 is made allows elastic deformation of hole 29 such that the inner surface of hole 29 pops into groove 36. This arrangement attaches rotatable member 34 to container 24 while allowing rotatable member 34 to be rotated relative to container 24.

FIG. 6 is a vertical cross-sectional diagram of a twist-up container with a crystalline deodorant structure according to the present invention inserted therewithin. In order to insert the oval stick crystalline deodorant 11 within container 24, the imbedded insert 17 is fitted over stem 32 and rotatable member 34 is rotated in a first direction. The action of the external threads 35 and internal threads 22 operate to draw the oval stick deodorant 11 within container 24 until the oval stick deodorant 11 is fully inserted within container 24. Cap 26 may then be placed on container 24 completing the assembly shown in FIGS. 6 and 7. In order to raise the oval stick deodorant 11, the cap 26 is removed and rotatable member 34 is turned in a second direction, opposite to the first direction. The inner oval or ellipsoidal shape of container 24 serves to prevent rotation of the oval stick deodorant 11 when rotatable member 34 and its stem 32 are rotated thereby causing the oval deodorant stick 11 to be raised or lowered within container 24. Container 24 includes at least a single aperture for permitting drainage of any water in the container 24. According to one embodiment, bottom end 27 includes first and second apertures 27' and 27" in container 24 to enable such drainage of water.

Figure 8:
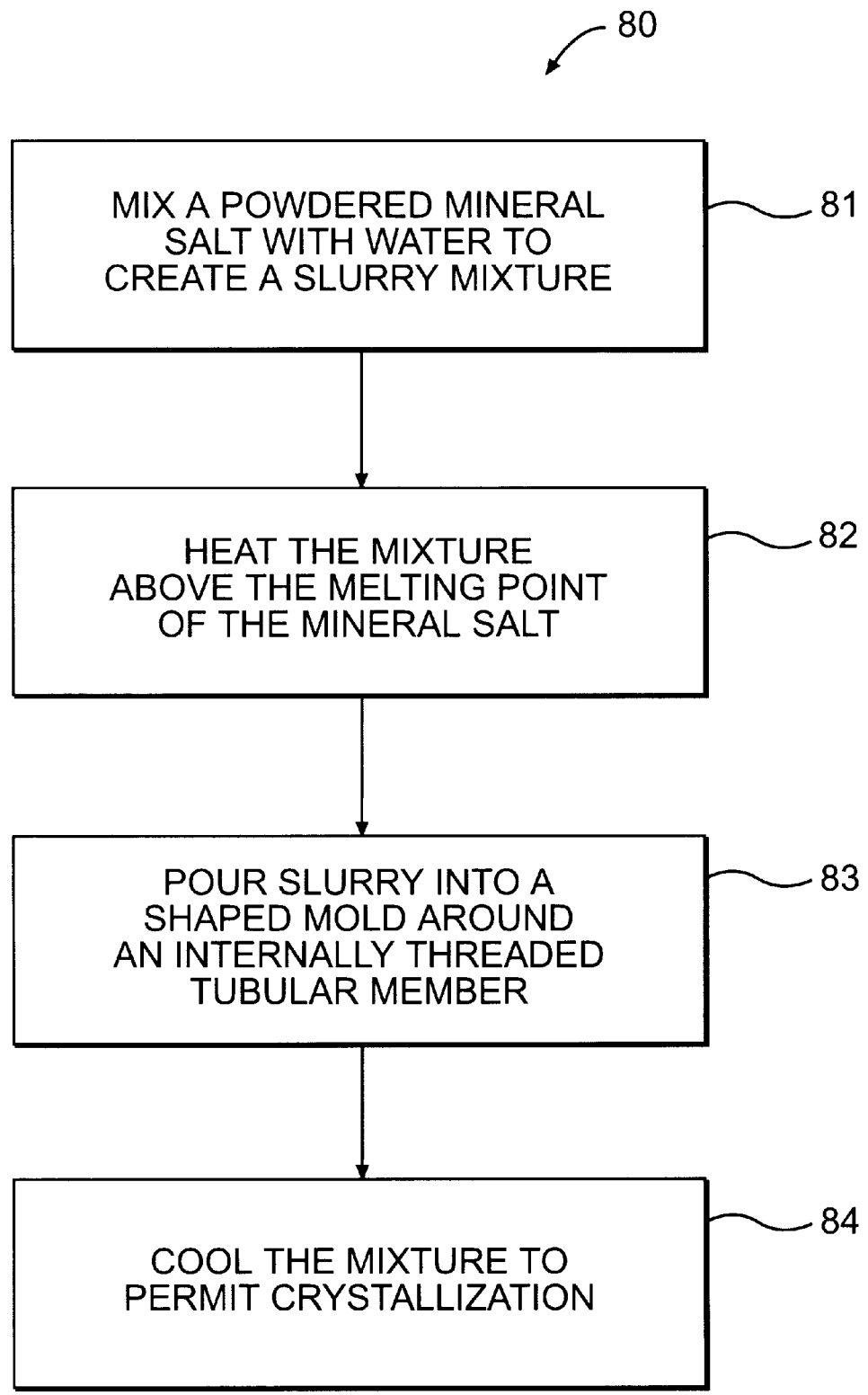
FIG. 8 is a flow chart of a method according to the present invention.

FIG. 8 is a flow chart of a method 80 according to the present invention. In particular, according to FIG. 8, a crystalline deodorant is manufactured by mixing 81 a powdered mineral salt with water to create a slurry. Next, the slurry is heated 82 raising the temperature of said mixture above the melting point of said mineral salt. Then, the resultant slurry mixture is poured 83 into a mold of selected shape around an internally threaded tubular member, and thereafter, the melted mixture is cooled 84 and allowed to crystalize into its final predetermined form.

While the above described and illustrated invention has been shown in terms of a specific embodiment which has been shown to operate in a most satisfactory manner, the invention is not to be limited to the particular embodiment shown and described. Rather, any obvious changes which perform or function in the same way to achieve substantially the same result are intended to be included within the scope of the claims appended hereto.

It is claimed as follows:

1. A crystalline deodorant having a bottom surface, a top surface and a side surface, said side surface having an oval shape in a direction transverse to a longitudinal axis between the top and bottom surfaces; and an internally threaded insert imbedded in said crystalline deodorant in a direction in line with said longitudinal axis.

2. The crystalline deodorant of claim 1, including a container proportioned to fit said crystalline deodorant therewithin and a rotational member attached to said container and connected to the threads of said insert.

3. The deodorant of claim 2 wherein said rotational member comprises a stem attached to a rotatable disk, said rotatable member being attached to said container, said stem having screw threads which threadingly mate with said threaded insert, said threaded stem extending within said container and said crystalline deodorant in line with said longitudinal axis and said rotatable disk fitting within a crevice located at a closed end of said container.

4. A method for manufacturing a crystalline deodorant comprising the steps of:
   mixing a powdered mineral salt with water;
   raising the temperature of said mixture above the melting point of said mineral salt;
   pouring said mixture into a mold having a desired shape; placing an internally threaded insert in line with a direction to be the longitudinal axis within said mixture; and
   allowing said melted mixture to cool and crystallize.

5. The method of claim 4 including the step of grinding a crystallized mineral salt into a powder.

6. The method of claim 5 including the step of removing the solidified crystalline deodorant from said mold.

7. The method of claim 4 wherein said mineral salt comprises potassium alum.

8. A method for manufacturing an oval shaped crystalline deodorant comprising the steps of:
   mixing a powdered mineral salt with water at room temperature;
   raising the temperature of said mixture above the melting point of said salt;
   pouring said mixture into a mold having the oval shape; placing an internally threaded insert in line with a direction to be the longitudinal axis within said mixture; and
   allowing said mixture to cool and crystallize.

9. The method of claim 8 including the step of removing the crystallization from the mold.

10. The method of claim 8 wherein said mineral salt comprises potassium alum.

11. A unitary deodorant bar having a bottom surface, a top surface and a side surface, said side surface having a rounded shape in a direction transverse to a longitudinal axis between the top and bottom surfaces, wherein said unitary deodorant bar is formed smoothly around all but a lower extension of an internally threaded tubular member imbedded in said deodorant bar in a direction in line with said longitudinal axis adapted to receive insertion of a complementary male threaded member.

12. The deodorant according to claim 11 held in a hollow receiving container having an internal recess adapted to slidingly fit over said crystal deodorant.

13. The deodorant according to claim 12 comprising an insertable member axially secured to said container and being complementarily threaded to engage the inner threads of said tubular member for rotational engagement.

14. The deodorant of claim 13 wherein said insertable member includes a stem attached to a rotatable disk, said rotatable member being attached to said container.

15. A method for manufacturing a deodorant comprising:
   mixing a powdered mineral salt with water;
   raising the temperature of said mixture above the melting point of said mineral salt;
   pouring said mixture into a mold having a desired shape; placing an internally threaded insert in line with a direction to be the longitudinal axis within said mixture; and
   cooling said melted mixture.

16. A method for manufacturing a shaped deodorant comprising:
   mixing a powdered mineral salt with water at room temperature;
   raising the temperature of said mixture above the melting point of said salt;
   pouring said mixture into a mold having an elongated shape; placing an internally threaded insert in line with a direction to be the longitudinal axis within said mixture; and
   allowing said mixture to cool and crystallize.

17. The deodorant according to claim 12 wherein said hollow receiving container defines at least a single aperture for permitting drainage of any water in said hollow receiving container.

18. A method for manufacturing a shaped, solid crystalline deodorant comprising:

mixing a powdered mineral salt with a solvent to create a slurry;

raising the temperature of said slurry above the melting point of said mineral salt;

pouring said raised temperature slurry into a mold having a desired shape; placing an internally threaded insert in line with a direction to be the longitudinal axis within said mixture; and allowing said poured slurry to cool and crystallize.

19. The method of claim 18 wherein said solvent is water.

20. The method of claim 18 wherein said mineral salt comprises potassium alum.

* * * * *